(12) United States Patent
Ainger et al.

(10) Patent No.: US 6,610,280 B2
(45) Date of Patent: Aug. 26, 2003

(54) HAIR TREATMENT COMPOSITIONS

(75) Inventors: Nicholas Ainger, Wirral (GB); Peter Fairley, Le Meux (FR)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/117,639

(22) Filed: Apr. 5, 2002

(65) Prior Publication Data

US 2002/0182161 A1 Dec. 5, 2002

(30) Foreign Application Priority Data

Apr. 6, 2001 (EP) .............................. 01303267

(51) Int. Cl.$^7$ ............................ A61K 7/11; A61K 7/075
(52) U.S. Cl. ................ 424/70.12; 424/70.1; 424/70.27; 424/70.31; 424/70.11; 424/70.19; 424/70.121; 424/70.122; 424/70.28; 424/70.17; 424/70.21
(58) Field of Search ............................ 424/70.1, 70.12, 424/70.27, 70.31, 401, 70.11, 70.19, 70.121, 70.122, 70.17, 70.21, 70.28; 514/937

(56) References Cited

U.S. PATENT DOCUMENTS

| | | | |
|---|---|---|---|
| 6,028,031 A | | 2/2000 | Gamblin et al. |
| 6,028,041 A | * | 2/2000 | Decoster et al. ............. 510/119 |
| 6,048,519 A | * | 4/2000 | Hiraishi et al. ......... 424/70.122 |
| 6,177,090 B1 | * | 1/2001 | Dubief et al. ................ 424/401 |
| 6,194,363 B1 | * | 2/2001 | Murray ........................ 510/119 |

FOREIGN PATENT DOCUMENTS

| | | |
|---|---|---|
| EP | 0811371 A2 | 4/1997 |
| GB | 2289686 | 11/1995 |
| WO | 97/12594 | 4/1997 |
| WO | 98/18443 | 5/1998 |
| WO | 98/43599 | 10/1998 |
| WO | 99/34768 | 7/1999 |
| WO | 99/44565 | 9/1999 |
| WO | 99/44567 | 9/1999 |
| WO | 99/49836 | 10/1999 |
| WO | 99/53889 | 10/1999 |

* cited by examiner

Primary Examiner—Thurman K. Page
Assistant Examiner—Blessing Fubara
(74) Attorney, Agent, or Firm—Michael P. Aronson

(57) ABSTRACT

A hair treatment composition containing a silicone component comprising droplets of silicone blend, the silicone blend comprising (i) from 50 to 95% by weight of the silicone component of a first silicone having a viscosity of at least 100,000 mm2/sec at 25° C., and (ii) from 5 to 50% by weight of the silicone component of a second silicone which is functionalised.

15 Claims, No Drawings

HAIR TREATMENT COMPOSITIONS

TECHNICAL FIELD

This invention relates to hair treatment compositions containing particular types of silicone blends which can provide the composition with conditioning benefits.

BACKGROUND AND PRIOR ART

The use of silicones as conditioning agents in hair treatment compositions is well known, and widely documented in the patent literature. Generally, dispersed droplets of silicone are suspended in the composition which, when applied to the hair, deposits the silicone material on the hair shaft resulting in the formation of a film. Whilst their use gives excellent conditioning, for example wet comb properties, there are several negatives associated with the use of silicones in hair treatment compositions. For example, repeated use of these compositions can lead to a build up of silicone and undesirable affects such as a heavy, oily feel to the hair.

There is therefore a need for hair treatment compositions which can provide conditioning benefits to the hair without the associated negatives, e.g. adversely affecting the clean feel of the hair.

WO99/44565 and WO99/44567 (Unilever) disclose shampoo compositions containing a combination of an amino-functionalised silicone and an insoluble non-amino functional insoluble silicone. In WO99/44565, the particle size of the non-amino functional silicone is less than 2 microns. In WO99/44567, the non-amino functional silicone has a viscosity of at least 500,000 cst. In both documents, the two silicone components are incorporated into the shampoo composition as separate emulsions.

WO99/49836 (Unilever) discloses rinse-off conditioner formulations containing an amino-functional silicone corresponding to a defined general formula and having a mole percent amino functionality of at least 1 mole %. The formulations may further comprise emulsified particles of a non-amino functionalised silicone.

WO99/53889 (Unilever) discloses shampoo compositions containing emulsified particles of a first insoluble silicone having a particle size of from 0.15 to 30 microns and a second insoluble silicone having a particles size less than 0.10 microns. The silicones are incorporated into the shampoo as preformed aqueous emulsions.

WO97/12594 (L'Oreal) describes hair compositions containing at least one silicone-grafted polymer with a polysiloxane backbone grafted by non-silicone organic monomers and at least one silicone selected from silicones containing a quaternary amine function, silicone resins and silicone gums.

U.S. Pat. No. 6,028,031 (L'Oreal) and EP 0 811 371 (L'Oreal) disclose the use of a mixture of at least one aminated silicone and at least one insoluble silicone of viscosity less than or equal to 100 Pa.s at 25° C. (100,000 cSt) in conditioning hair-care compositions.

WO98/18443 (Procter & Gamble) discloses shampoo compositions containing a first non-volatile conditioning agent of particle size less than 2 μm and a second non-volatile conditioning agent of particle size greater than 5 μm. The non-volatile conditioning agents may be silicones.

None of the above prior art documents disclose the use of intimate blends of combinations of silicones which result in individual particles comprising a mixture of silicones. In contrast, they describe addition of emulsions of each of the constituent silicone components separately to the hair compositions.

WO98/43599 (Unilever) discloses a hair treatment composition, such as a shampoo or conditioner, comprising a silicone component comprising (i) 0.01 to 50% by weight of a silicone gum having a viscosity greater than 1 McSt, (ii) 30 to 95% by weight of a silicone fluid having a viscosity of less that 100 kcSt, and (iii) 0.1 to 10% by weight of an amino functionalised silicone. The silicone component is preferably added as a single blend which may be in the form of a silicone mixture which is added to the composition during manufacture or alternatively it may be in the form of an aqueous emulsion which is added to the composition during manufacture.

We have surprisingly found that an intimate blend comprising a combination of a first silicone having a viscosity of at least 100,000 m$^2$/sec and a second silicone which is functionalised can be used in hair treatment compositions to provide excellent conditioning benefits. In contrast to the teaching of WO98/43599, it is not necessary to have a third silicone fluid component in order to achieve the benefit of improved conditioning.

SUMMARY OF THE INVENTION

In a first aspect, this invention provides a hair treatment composition containing a silicone component comprising droplets of silicone blend, the silicone blend comprising
  (i) from 50 to 95% by weight of the silicone component of a first silicone having a viscosity of at least 100,000 mm/sec at 25° C., and
  (ii) from 5 to 50% by weight of the silicone component of a second silicone which is functionalised.

DETAILED DESCRIPTION OF THE INVENTION

Unless specified otherwise, all wt. % values quoted hereinafter are percentages by weight based on total weight of the hair treatment composition.

As used hereinafter, the term "first silicone" refers to component (i) of the silicone blend, i.e. the silicone having a viscosity of at least 100 000 mm2/sec at 25° C., and the term "second silicone" refers to component (ii) of the silicone blend, i.e. the silicone which is functionalised.

Silicone Component

The total silicone content of the composition of the invention is suitably in the region of from 0.1 to 20%, preferably from 1 to 10 wt. %.

Suitably, the first silicone is present in an amount of at least 50 wt. % based on the total silicone content of the silicone component of the hair treatment composition and the second silicone is present in an amount of at least 5 wt. % based on the total silicone content of the silicone component of the hair treatment composition.

The silicone component of the composition is provided as a single blend which is added to the composition during manufacture. This single blend may simply be in the form of a silicone mixture which can be added to the composition during manufacture.

However, it is preferred that the single blend is in the form of an aqueous emulsion which is added to the composition during manufacture. Pre-formed aqueous emulsions of silicone may have advantages in that they themselves may be easier to handle or process than the "raw" silicone ingredients of the silicone component.

In any event, when added to the hair treatment composition, the silicone component becomes the internal phase of an emulsion which itself constitutes the hair treatment composition, and which is preferably water based.

A further feature of the invention is that the silicone present in the composition, when added as an already homogenised mixture, will be present in the hair treatment composition as a homogeneous mixture of silicones. That is, each silicone droplet in the composition will have essentially the same composition and will comprise a mixture (typically a solution) of the two types of silicone which together make up the silicone component of the composition, i.e. first silicone and second silicone.

Suitably, the weight ratio of the first silicone to the second silicone in the silicone component is in the range from 15:1 to 1:1, preferably from 10:1 to 1:1, more preferably from 8:1 to 1:1, and yet more preferably from 6:1 to 2:1. A particularly preferred ratio is 3:1.

First Silicone

The first silicone is present at a level of at least 50 wt. %, preferably at least 60 wt. % based on the total weight of the silicone component.

The first silicone has a viscosity of at least 100,000 mm2/sec at 25° C., preferably at least 200,000 mm2/sec at 25° C., more preferably at least 400,000 mm2/sec at 25° C.

In a preferred embodiment, the first silicone is a silicone gum and has a viscosity of at least 500,000 mm2/sec at 25° C., more preferably at least 600,000 mm2/sec at 25° C., and yet more preferably at least 1,000,000 mm2/sec at 25° C.

Suitably, the first silicone has a molecular weight of at least 100,000 Dalton, and preferably at least 200,000 Dalton. When the first silicone is gum, the molecular weight is suitably at least 400,000 Dalton, preferably at least 500,000 Dalton, and more preferably at least 550,000 Dalton.

Suitable as the first silicone are polydiorganosiloxanes, preferably derived from suitable combinations of $R_3SiO_{0.5}$ and $R_2SiO$ units, where each R independently represents an alkyl, alkenyl (e.g. vinyl), alkaryl, aralkyl or aryl (e.g. phenyl) group. R is most preferably methyl. Thus, preferred first silicones for use in the silicone component of compositions of the invention are polydimethylsiloxanes (which have the CTFA designation dimethicone), optionally having end groups such as hydroxyl. Good results have been obtained with dimethicone.

Suitable materials include DC-200 (ex Dow corning). Suitable silicone gums include SE30, SE54 and SE76 (ex General Electric Silicones).

The first silicone is not functionalised.

Second Silicone

The second silicone is present at a level of at least 5 wt. %, preferably at least 10 wt. %, and more preferably at least 15 wt. % based on the total weight of the silicone component.

Suitably, the second silicone has a viscosity of less than 500,000 mm2/sec at 25° C., preferably less than 400,000 mm2/sec at 25° C., more preferably less than 200,000 mm2/sec at 25° C.

Suitably, the second silicone has a molecular weight less than 200,000 Dalton, preferably less than 100,000 Dalton, more preferably in the range from 1 to 80,000 Dalton.

The second component of the silicone blend is a functionalised silicone. Suitable functionalised silicones include, for example, amino-, carboxy-, betaine-, quaternary ammonium-, carbohydrate-, hydroxy- and alkoxy-substituted silicones.

Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the present invention. However, a polydimethylsiloxane have hydroxyl substitutions along the polymer chain is considered a functionalised silicone. Preferred functionalised silicones are amino-functionalised silicones. Suitable amino functionalised silicones are described in EP 455,185 (Helene Curtis) and include trimethylsilylamodimethicone as depicted below, and are sufficiently water insoluble so as to be useful in compositions of the invention:

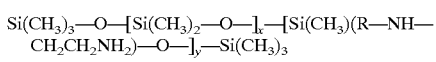

wherein x+y is a number from about 50 to about 500, and the mole % amine functionality is in the range of from about 0.3 to about 8%, and wherein R is an alkylene group having from 2 to 5 carbon atoms. Preferably, the number x+y is in the range of from about 100 to about 300, and the mole % amine functionality is in the range of from about 1.5 to about 6%.

Examples of amino-functionalised silicones useful in the silicone component of the composition of the invention are Q2-8220 and Q2-8466 fluids, available from Dow Corning, and also SF-1708-D1, available from General Electric Silicones.

Suitably, the amino-functionalised silicones have a mole percent amino functionality in the range from 0.3 to 8, preferably from 0.5 to 4.

The viscosity of silicones can be measured by means of a glass capillary viscometer as set out further in Dow Corning Corporate Test Method CTM004, Jul. 20 1970.

As described above, the silicone component of the composition is provided as a single blend which is added to the composition during manufacture. This single blend may simply be in the form of a silicone mixture which can be added to the composition during manufacture.

However, it is highly preferred that the blend be in the form of an aqueous emulsion which may itself be added to the composition during manufacture. Preferably, the aqueous emulsion is mechanically-formed. In such emulsions, it is preferable that the emulsion additionally includes at least one emulsifier in order to stabilise the silicone emulsion.

Suitable emulsifiers are well known in the art and include anionic and nonionic surfactants. Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers for the silicone particles are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Preferably, the $D_{3,2}$ average particle size of the silicone droplets in the emulsion and also in the final composition is less than 100 μm, more preferably less than 20 μm, and yet more preferably less than 10 μm. Preferably, the average particle size of the silicone droplets in the emulsion and also in the final composition is greater than 0.1 μm. A smaller silicone particle size enables a more uniform distribution of silicone on the hair for the same amount of silicone in the composition.

The particle size parameter, $D_{3,2}$, is the well known Sauter mean diameter which is discussed in *Size Measurement of Particles* in the Encyclopedia of Chemical Technology, Volume 22, pages 56–60, John Wiley, 1997. This parameter is defined as (Equation 6 in the above reference):

$$D_{3,2} = \Sigma n_j d_j^3 / \Sigma n_j d_j^2$$

where $n_j$ is the number of particles having diameter $d_j$.

Silicone particle size may be measured by means of a laser light scattering technique, for example using a 2600D Particle Sizer from Malvern Instruments.

A particularly suitable emulsion for use as the silicone component of the composition of the invention is a preformed emulsion containing the first silicone, especially a silicone gum, the second silicone, especially an amino-functionalised silicone, in a nonionic surfactant base, of silicone particle size 3 μm.

Hair treatment compositions according to the invention may suitably take the form of shampoos, conditioners, sprays, mousses or lotions. Preferred hair treatment composition forms are shampoos, conditioners and mousses.

Preparation of Aqueous Silicone Blend Emulsions

A preferred process for preparing aqueous emulsions of the single silicone blend which can then be incorporated in the hair treatment compositions involves use of a high-shear mixer. Suitable mixers should be capable of handling high viscosity materials at low temperatures. Preferably, the mixer is a hollow cylinder or bowl-shaped and comprises a centrally-mounted rotatable shaft carrying thereon tools or blades which rotate with the shaft.

Suitably, the clearance of the tips of the tools or blades from the wall of the mixer is relatively small, e.g. less than 20 mm, preferably less than 15 mm, more preferably less than 10 mm. The speed of rotation of the shaft will vary depending on the dimensions of the mixer but will typically be in the region of 10–120 rpm.

Preferably, the mixer is also capable of being actively cooled, e.g. it comprises a jacket through which a cooling fluid can be circulated.

A preferred process, which is especially applicable when the first silicone is a gum, is as follows:

The first silicone is added to a mixer (e.g. a 2Z Winkworth laboratory z-blade) operating at a slow blade speed. The second silicone is then added to the first silicone in the mixer in small portions. After each portion of second silicone is added, mixing is continued and a portion of emulsifying surfactant is added to the mixer which helps the first and second silicones blend. At the temperature of operation, the emulsifying surfactant should not be a liquid, e.g. it is preferably paste-like. Suitably, the emulsifying surfactant is a nonionic surfactant. Mixing at slow speed is continued until the mixture is substantially homogeneous and only then is a further portion of second silicone added to the mixer and the procedure repeated until all the second silicone material has been added.

The speed of the mixer is then increased and a co-emulsifier may be added at this point. The mixture should now consist of discrete lumps of the silicone blend and mixing should be continued until the lumps remain a constant size.

Water is added slowly to the mixture, preferably as a solution containing a thickening agent, e.g. cellusize. The thickening solution may be in the form of a thick gel when added to the mixer. As water is added, the mixture will invert and become a homogenous mix. At this stage, the mixture should be left to mix without further addition of water to obtain a narrow particle size distribution. The remaining water, e.g. thickener solution is then added is small aliquots.

Finally, the pH of the emulsion may be adjusted as appropriate and other minor ingredients may be added.

It is important that the temperature of the mix does not become too high throughout the process as this can cause the first silicone, especially when it is a silicone gum, to separate of the emulsion. In addition, higher temperatures during the blending process can lead to problems, e.g. it is preferable that the emulsifying surfactant added after each addition of second silicone does not become liquid as this will not blend efficiently with the silicone mixture. For this reason, the mixer should be constantly cooled to, for example, a temperature below 40° C., preferably below 30° C.

Shampoo Compositions

A particularly preferred hair treatment composition in accordance with the invention is a shampoo composition.

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 wt. %.

The shampoo composition can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt. %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 wt. %.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

The shampoo composition may also optionally include one or more cationic co-surfactants included in an amount ranging from 0.01 to 10, more preferably from 0.05 to 5, most preferably from 0.05 to 2 wt. %.

The total amount of surfactant (including any co-surfactant, and/or any emulsifier for the silicone component) in shampoo compositions of the invention is generally from 0.1 to 50, preferably from 5 to 30, more preferably from 10 to 25 wt. %.

Cationic Deposition Polymer

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides(as described in WO95/22311).

Other cationic deposition polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

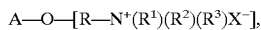

A—O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives.

Particularly preferred deposition polymers are JAGUAR C13S, JAGUAR C15, JAGUAR C17 and JAGUAR C16 and JAGUAR C162.

Conditioners

Compositions in accordance with the invention may also be formulated as conditioners for the treatment of hair (typically after shampooing) and subsequent rinsing.

Conditioning Surfactant

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g. chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

Salts of primary, secondary, and tertiary fatty amines are also suitable cationic surfactants. The alkyl groups of such amines preferably have from about 12 to about 22 carbon atoms, and can be substituted or unsubstituted.

Particularly useful are amido substituted tertiary fatty amines. Such amines, useful herein, include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to H$^+$ from the acid is preferably from about 1:0.3 to 1:1.2, and more preferably from about 1:0.5 to about 1:1.1.

In conditioners of the invention, the level of cationic surfactant is preferably from 0.01 to 10, more preferably 0.05 to 5, most preferably 0.1 to 2 wt. % of the total composition.

Fatty Alcohol

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10, preferably from 0.1 to 5 wt. % by weight of the total composition. The weight ratio of cationic surfactant to fatty alcohol is suitably from 10:1 to 1:10, preferably from 4:1 to 1:8, optimally from 1:1 to 1:4.

Mousses

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from 3 to 30, preferably from 5 to 15 wt. % of the total composition.

Small quantities of surfactant ranging anywhere from 0.1 to 10, preferably from 0.1 to about 1 wt. %, for example 0.3 wt. % may be present in the hair mousse compositions of the invention. The surfactant may be an anionic, nonionic or cationic emulsifier. Particularly preferred are nonionic emulsifiers which are formed from alkoxylation of hydrophobes such as fatty alcohols, fatty acids and phenols.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5 wt. % of the total composition.

Preferably, compositions of this invention also contain adjuvants suitable for hair care. Generally such ingredients are included individually at a level of up to 2, preferably up to 1 wt. % of the total composition.

Among suitable hair care adjuvants, are:
(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Mode of Use

The compositions of the invention are primarily intended for topical application to the hair and/or scalp of a human subject to improve hair fibre surface properties such as smoothness, softness, manageability, cuticle integrity, and shine.

The invention will now be further illustrated by the following, non-limiting Examples:

EXAMPLES

Example 1

The following silicone blend emulsion, suitable for incorporation into a hair treatment composition was prepared:

| Ingredient | Weight (g) |
|---|---|
| High viscosity silicone gum (Gum Y) | 262.5 |
| Low viscosity amino-functionalised silicone (Amino B) | 87.5 |
| Synperonic 13/15 | 122.5 |
| Lauryl alcohol (Condea Nafol 1214) | 7.0 |
| Sodium benzoate | 3.5 |
| Cellusize QP30000H | 7.0 |
| Soft water | 210 |
| Hydrochloric acid | to pH 4–5 |
| Kathon CG | 0.7 |
| | 700 g sample |

The silicone emulsion was made using a model 2z Winkworth laboratory z-blade which was cooled through with water to keep the batch below 30° C. The rear blade was run at approximately 32 rpm and the front blade was run at between 19 and 95 rpm.

The silicone gum was added to the mixer, the front blade running at a slow speed. 10 g of amino silicone was then added to the mixing gum, followed by 10 g of Synperonic 13/15 (which was in paste form) and the mixing continued until the mixture was homogenous. This process of addition was repeated until all the amino silicone had been added.

Any remaining Synperonic was then added to the mixer and mixing continued until the mixture was homogenous.

The lauryl alcohol was then added to the mixture and the speed of the front blade increased. Mixing was continued until the "lumps" remained a constant size.

The sodium benzoate was added to the mixer.

The cellusize (thickener) was mixed with the soft water in a Silverston mixer and mixed until a thick gel formed. The thickener solution was then slowly added to the mixture in the z-blade mixer and until the mixture inverted and became a homogenous mix. At this point, no more thickener solution was added and the mixture was left to mix for a while to ensure a narrow and desired particle size distribution. The remainder of the thickener solution was then added in small aliquots and finally the acid added to a pH of 4–5, followed by the Kathon.

Using the above process of manufacture, shampoo compositions comprising the following blends of silicone gums and amino-functionalised silicones were prepared.

| Shampoo composition | Silicone gum | Amino-silicone | Weight ratio (gum:amino) |
|---|---|---|---|
| I | X | B | 1:1 |
| II | Y | A | 1:1 |
| III | Y | B | 3:1 |
| IV | X | A | 3:1 |
| V | Y | A | 3:1 |
| VI | X | B | 3:1 |

Gum X: MW 525,000–675,000
Straight polydimethylsiloxane
Gum Y: MW 750,000–850,000
Straight polydimethylsiloxane
Amino A: MW 116,000
Amino branch: $-(CH_2)_2-O-(C_5NH_5(CH_3)_4)$; $C_5NH_5$ is an azo ring.
0.2 mole % amino functionality
Amino B: MW 32,000
Amino branch: $-(CH_2)_3-NH-CH_2-NH_2$
0.75 mole % amino functionality Example 2

Shampoo composition III from Example 1 was assessed in a panel test with three other shampoo compositions, compositions A, B and C.

Composition A was a normal variant commercial shampoo containing an amino-silicone emulsion (DC-949) and a high MW PDMS (DC-1784), the two silicones being added separately to the shampoo.

Composition B was a shampoo composition made as described in Example 1, except that the amino-functionalised silicone was substituted by a non-functionalised PDMS fluid. The ratio of silicone gum to PDMS fluid was 3:1.

Composition C was a shampoo composition similar to those described in Example 1, except that the only silicone present was a PDMS silicone gum emulsion.

About 160 women who had normal or greasy hair of medium or fine texture were each given 60 ml plastic bottles of each of the four shampoo compositions to use over a four week period. Each product was used at least twice (and a maximum of four times), and only one product was used in any one week. The panellists used the test product in place of their normal shampoo according to their normal habit and refrained from using conditioner or conventional mousse on the same day that they used the test product. The test was balanced so that equal numbers of panellists used each product each week. At the end of each week, each panellist completed a questionnaire scoring the shampoo tested that week against a series of attributes.

From the information received from the panellists, a series of seven attributes of shampoo compositions III, B and C could be compared against those of the commercial shampoo A. The significance rating scores are as follows:

* $p<0.10$
** $p<0.05$
*** $p<0.01$

Composition III beat composition A on:

| Attribute | Significance level |
|---|---|
| Wet-comb | *** |
| Softness | *** |
| Smooth-feel | ** |
| Shine | ** |
| Overall styling | ** |
| Bounce | ** |

Furthermore, there was no compromise on the clean-feel attribute, composition III beating composition A on this attribute but not to any level of significance.

Composition B beat composition A on smooth-feel (significance level *), but failed to show any significant benefit as regards the other six attributes.

Composition C beat composition A on wet-comb (significance level *), but failed to show any significant benefit as regards the other six attributes.

Conclusions

The results show that the Example III, a shampoo according to the invention, delivers improved results relative to the commercial comparative product A for important conditioning attributes without compromising the clean-feel.

In contrast, composition B and C, which are not shampoos according to the invention, failed to deliver improved results relative to the commercial comparative product A for the same conditioning attributes.

What is claimed is:

1. A hair treatment composition containing droplets comprising a silicone component, wherein the silicone component in each droplet consists of:

(i) from 50 to 95% by weight of the silicone component of a first silicone having a viscosity of at least 100,000 mm2/sec at 25° C., and (ii) from 5 to 50% by weight of the silicone component of a second silicone which is functionalised.

2. A composition as claimed in claim 1, wherein the first silicone is a gum and has a viscosity of at least 500,000 mm2/sec at 25° C.

3. A composition as claimed in claim 1, wherein the second silicone has a viscosity of less than 500,000 mm2/sec at 25° C.

4. A composition as claimed in claim 1, wherein the first silicone has a molecular weight of at least 200,000 Daltons.

5. A composition as claimed in claim 1, wherein the second silicone has a molecular weight of less than 200,000 Daltons.

6. A composition as claimed in claim 1, wherein the silicone component has an average $D_{3,2}$ particle size in the range from 0.01 to 100 µm.

7. A composition as claimed in claim 1, wherein the silicone content in the hair treatment composition is in the range of from 0.1 to 20 wt. %.

8. A composition as claimed in claim 1, wherein the first silicone is a polydimethylsiloxane.

9. A composition as claimed in claim 1, wherein the second silicone is an amino-functionalised silicone.

10. A composition as claimed in claim 9, wherein the amino-functionalised silicone has a mole percent amino functionality in the range from 0.3 to 8.

11. A composition as claimed in claim 1, wherein the weight ratio of the first silicone to the second silicone in the silicone component is in the range from 15:1 to 1:1.

12. A composition as claimed in claim 1, wherein the silicone component is in the form of a mechanical emulsion.

13. A composition as claimed in claim 1, which is a shampoo composition comprising at least one cleansing surfactant selected from anionic, amphoteric and zwitterionic surfactants and mixtures thereof, and further comprising a cationic deposition polymer.

14. A composition as claimed in claim 1, which is a conditioner composition comprising at least one conditioning surfactant and a fatty alcohol and/or an alkoxylated fatty alcohol.

15. A composition as claimed in claim 9, wherein the amino-functionalised silicone has a mole percent amino functionality in the range from 0.5 to 4.

* * * * *